United States Patent [19]
Bruscato et al.

[11] 4,086,335
[45] Apr. 25, 1978

[54] PHARMACEUTICAL TABLETS CONTAINING CHITIN AS A DISINTEGRANT

[76] Inventors: Frank N. Bruscato, 2209 Fannie St.; August G. Danti, 2211 Ann St., both of Monroe, La. 71201

[21] Appl. No.: 626,988

[22] Filed: Oct. 29, 1975

[51] Int. Cl.$^2$ ............ A61K 31/70; A61K 47/00
[52] U.S. Cl. .................... 424/180; 424/361
[58] Field of Search .................. 424/180, 361

[56] References Cited

U.S. PATENT DOCUMENTS

| | | | |
|---|---|---|---|
| 3,181,998 | 5/1965 | Kanig | 424/361 |
| 3,257,275 | 6/1966 | Weisberg et al. | 424/180 |
| 3,632,754 | 1/1972 | Balassa | 424/180 |
| 3,725,556 | 4/1973 | Hanssen et al. | 424/361 |
| 3,879,377 | 4/1975 | Austin | 424/180 |
| 3,903,268 | 9/1975 | Balassa | 424/180 |
| 3,911,116 | 10/1975 | Balassa | 424/180 |
| 3,914,413 | 10/1975 | Balassa | 424/180 |

Primary Examiner—Stanley J. Friedman
Attorney, Agent, or Firm—George F. Helfrich

[57] ABSTRACT

A pharmaceutically-active ingredient is thoroughly mixed with from about 2 to about 20 percent by weight of chitin, and the mixture is fabricated into a tablet by standard means such as direct compression or wet granulation techniques. The tablet exhibits highly beneficial disintegration properties.

2 Claims, No Drawings

PHARMACEUTICAL TABLETS CONTAINING CHITIN AS A DISINTEGRANT

BACKGROUND OF THE INVENTION

1. Field of the Invention

The present invention relates generally to drug compositions. It relates in particular to drug compositions in the form of tablets containing the glucosamine polysaccharide chitin as a disintegrant.

2. Prior Art

A tablet disintegrant is a substance, or a mixture of substances, added to a tablet to facilitate its break up or disintegration after administration. Starches are the most widely used tablet disintegrants. In addition to starches, a large variety of materials have been used and reported to be effective as tablet disintegrants. Such substances include veegum HV [Gross, H. M., and C. H. Becker. "A Comparative Study of Tablet Disintegrating Agent," *J. Amer. Pharm. Assoc., Sci. Ed.*, 41:157 (1952).]; methylcellulose, agar [Firouzabadian, A., and C. I. Huyck. "Some Recently Developed Chemicals as Disintegrating Agents for Compressed Tablets," *J. Amer. Pharm. Assoc., Sci. Ed.*, 43:248 (1954).]; bentonite [Granberg, C. B., and B. E. Benton. "The Use of Dried Bentonite As A Disintegrating Agent in Compressed Tablets of Thyroid," *J. Amer. Pharm. Assoc., Sci. Ed.*, 36:648 (1949).]; cellulose product [Fakouhi, T. A., et al. "Wood Products, Corncob, and Cellulose as Tablet Disintegrating Agents," *J. Pharm. Sci.*, 52:700 (1963).]; [Bequette, R. J., and C. L. Huyck. "Tablet Disintegration with Cellulose," *Drug Cosmetic Ind.*, 81:166 (1957).]; natural sponge [Crisafi, R. C., and C. H. Becker. "A Study of Natural Sponge As A Disintegrating Agent in Compressed Tablets," *J. Amer. Pharm. Assoc., Sci. Ed.*, 47:363 (1958).]; cation-exchange resin [Van Abbe, N. J., and J. T. Rees. "Amberlite Resin XE-88 As A Tablet Disintegrant," *J. Amer. Pharm. Assoc., Sci. Ed.*, 47:487 (1958).]; alginic acid [Gerding, T. G., and Dekay, H. G. "Alginic Acid and Its Derivatives as Binding and Disintegrating Agents in Tablet Manufacture," *Drug Std.*, 23:132 (1955).]; and guar gum [Eatherton, L. E., et al. "Guar Gum As A Binder and Disintegrator for Certain Compressed Tablets," *Drug Std.*, 23:42 (1955).] among others.

Notwithstanding the asserted efficacy of these and similar materials as tablet disintegrants, they are found wanting for one or more reasons, of which the following are exemplary: high cost; merely moderate efficiency; potential deterioration resulting in decreased utility after long periods of storage; possible adverse effects upon the pharmaceutically-active ingredient comprising the major component of the tablet.

SUMMARY OF THE INVENTION

Accordingly, it is the primary object of this invention to provide a pharmaceutical tablet having a highly efficient, exceedingly economical, very stable and eminently compatible disintegrant.

This object is achieved, and the disadvantages of the prior art are obviated, by providing a pharmaceutical tablet comprising a pharmaceutically-active ingredient and from about 2 to about 20 percent by weight of chitin as a disintegrant. The pharmaceutical tablet advantageously comprises a water-soluble drug and from about 2 to about 20 percent by weight of chitin as a disintegrant. The water soluble drug is desirably one or more members of the group consisting of highly water-soluble drugs, moderately water-soluble drugs, slightly water-soluble drugs, and very slightly water-soluble drugs. An example of the highly water-soluble drug is sodium salicylate; an example of the moderately water-soluble drug is caffeine; an example of the slightly water-soluble drug is aspirin; and an example of the very slightly water-soluble drug is phenacetin. Very highly advantageous results are obtained when the chitin is present in the tablet in an amount sufficient to provide about 5 percent by weight. Beneficial results are obtained, however, when the amount of chitin present is as low as about 2 percent by weight. No advantage is envisioned if the amount of chitin exceeds about 20 percent by weight.

The desired pharmaceutically-active ingredient and chitin are thoroughly admixed in suitable proportions, and the resulting intimate mixture is fabricated into a tablet by standard means such as the direct compression or wet granulation techniques. Of course, any of a number of commonly employed tablet diluents and/or tablet lubricants may be utilized if desired or expedient.

DETAILED DESCRIPTION OF THE PREFERRED EMBODIMENTS

For a more complete understanding of the present invention, reference should be made to the description of the preferred embodiments, which is set forth in detail hereinbelow;

Chitin is a naturally occurring polymer of N-acetyl-D-glucosamine. It is found in the shells of crabs, crayfish, and other crustacea, as well as in the cell walls of some plants. In chemistry, it has been employed to remove impurities from aqueous medium, as an adsorbent for collection of metal ions from aqueous and organic solutions, in the separation of metal ions such as $UO_2^2$ from $Fe^{3+}$, $Ca^{2+}$, and $Mg^{2+}$, and in the chromatographic separation of amino acids. The sorption of DDT and its analogues on chitin has been reported, as have the adsorption of dyes and other organic solutes including non-ionic hydroxy compounds, and aromatic sulfonic acids and azo dyes. The chromatography of Tobacco Mosaic Virus on chitin was reported in 1961. In the pharmaceutical area, chitin has been reported describing its effect on the rate of wound healing in the body and as a bioerodible or drug release agent. Chitin has not been reported as a disintegrant in the preparation of tablets.

Chitin, a stable, leathery solid, is grayish-white in color. It is thermally stable to about 260° C, where it decomposes. Chitin is insoluble in organic solvents and will resist being dissolved by acids and bases. It exhibits no harmful effects on animals or humans.

The chitin used for this invention was obtained from Matheson Coleman & Bell, and was practical grade (Lot No. p9013). Starch (Lot No. 711548), magnesium stearate (Lot No. 713007), acetone (Lot No. 722638) were obtained from Fisher Scientific Company.

Sodium salicylate of prescribing and compounding grade (Lot No. 6732) was obtained from Mallinckroft Chemical Works. Aspirin powder was obtained from Merck & Co., Inc. (Lot No. 72740). Phenacetin was obtained from Matheson Coleman & Bell, and was chemical grade (Lot No. 5727). Caffeine was obtained from Eastman Organic Chemicals and was chemical grade (Lot No. 355).

Lactose for direct compression was obtained from Scheffield Chemical (Lot No. C-102-2). Lactose for wet granulation was obtained from Aldrich Chemical Co., Inc. (Lot No. L25-4).

n-Hexane was obtained from Curtin Scientific Co. (Lot No. 36033B). The stearic acid was obtained from Barker Chemical Co. (Lot No. 9333). The methanol was obtained from Barker Chemical Co. (Lot No. 9097).

The apparatus for testing the disintegration (Type ZT2) and the friabulator (Type TA3R) were obtained from ERWEKA (Chemical & Pharmaceutical Industry Co., Inc.). The spectrophotometer used in the dissolution studies was a Coleman 124, double beam spectrophotometer.

Experimental Methods

Purification of Practical Chitin

The practical chitin was placed in a U.S. Stoneware ball mill and ground until the particles of chitin passed through a No. 200 mesh U.S. Standard sieve. These particles were then collected and placed in a Soxhlet Extractor for washing with organic solvents. The small chitin particles were washed with n-hexane, acetone, and methanol. Each solvent was used continuously for 48 hours. The chitin was then dried under room temperature.

Direct Compression and Wet Granulation Tablet Formulations

Various tablet formulations exemplifying both direct compression and wet granulation techniques were selected to compare the disintegration, dissolution, and friability properties of the disintegrants under investigation. The material composition of these tablets is presented in Table I (for direct compression) and Table II (for wet granulation) with the categorizing of each tablet type into nine series.

Four drugs of varying water solubility were chosen for the direct compression method. These drugs excluding aspirin were also chosen for the wet granulation method.

Direct Compression Tablet Preparation for Disintegration Time Studies, Dissolution Rate, and Friability Tests The required amounts of drugs, tablet diluent, and disintegrant were accurately weighed and passed through a No. 20 mesh U.S. Standard sieve. The materials were then transferred to a Turbula Shaker Mixer and tumbled for ten minutes. The required amount of lubricant was accurately weighed, passed through a No. 60 mesh U.S. Standard sieve, and added to the shaker mixer. The materials were mixed for an additional five minutes. The materials were then compressed into tablets of appropriate weight and hardness, utilizing a rotary tablet machine equipped with selected size tablet punches. Five hundred tablets were made per batch. Two batches were made for each series of formulations.

Wet Granulation Tablet Preparation for Disintegration Time Studies, Dissolution Rate, and Friability Tests The required amount of drug, tablet diluent, and disintegrant was accurately weighed and passed through a No. 40 mesh U.S. Standard sieve. These materials were transferred to a Turbula Shaker Mixer and tumbled for 10 minutes. These materials were then made into mass by adding the binding solution, and the mass was granulated by hand by forcing the mass through a No. 8 mesh U.S. Standard sieve. These granules were dried in a fluid bed type dryer to a 1–3% moisture content. The dried granules were forced through a No. 16 mesh screen. The required amount of lubricant was accurately weighed, passed through a No. 60 mesh U.S. Standard sieve, and added to the granules. These materials were then mixed for 5 minutes by using the Turbula Shaker Mixer. The materials were then compressed into tablets of the appropriate weight and hardness, utilizing rotary machine equipped with selected size tablet punches.

Disintegration Test for Tablets Prepared to Evaluate Disintegrant

The USP XVIII test procedure for uncoated tablets was utilized and modified to the extent that no disks were employed. The volume of the container for the immersion fluid was 3500 ml. and the temperature was maintained at 37° ± 1° C by inserting a Scheco heater on the wall inside the container.

The term "disintegration" as used herein refers to the tablet breaking up or crumbling into a multitude of discrete particles and is not synonymous with solution. Disintegration is complete when substantially all the tablet particles are of a small enough size to pass through the No. 10 mesh screen on the basket.

Friability Test for Tablets Prepared to Evaluate Disintegrant

The friability of all tablets studied was determined by Roche Friabulator which consisted of a 27-cm. diameter, plexiglas hollow chamber, 3.7 cm. in width. A curved arm in the chamber extends from a point on the circumference to slightly above the center of the apparatus. The apparatus is rotated at 20 rpm by use of a shaft and motor at its center. The tablets were dropped a distance of 14 cm. from the arm at each rotation.

Twenty previously weighed tablets were placed in the apparatus, and the apparatus was then rotated for 5 minutes to subject the tablets to 100 drops. The tablets were then weighed and the weight loss was calculated in terms of percent friability.

Dissolution Rate Analysis of Tablets

The apparatus utilized is described in USP XVIII utilizing a 1000 ml. beaker as the immersion fluid container. A volume of 1000 ml. of aqueous 0.1N hydrochloric acid (pH 1.2, 37° ± 1° C) was used as the dissolution medium, and a stirring speed of 50 rpm was maintained.

Dissolution of the drug from the tablets was conducted through a thirty minute interval. The analysis following dissolution involved the withdrawal of 10 ml. aliquots at five minute intervals using a 10 ml. pipet. Then 10 ml. of aqueous fluid pH 1.2 which had been equilibrated at 37° C was added to the beaker to replace the withdrawn volume. The aliquot was filtered through filter paper and diluted to 25 ml. with aqueous fluid pH 1.2. The absorption of the diluted solution was measured on a spectrophotometer over the Ultra Violet spectrum. The maximum absorbance at 302 nm. was used for sodium salicylate, 275 nm. for aspirin, 283 nm. for caffeine, 245 nm. for phenacetin, to calculate the concentration in 10 ml. aliquots of each drug at a particular time interval. The concentration of drug in 1000 ml. dissolution medium at a particular time interval was calculated.

TABLE I

TABLET COMPOSITION USED TO COMPARE DISINTEGRATION TIME, DISSOLUTION RATE, AND FRIABILITY TEST FOR CHITIN AND STARCH EMPLOYING THE DIRECT COMPRESSION METHOD

| | Quantity per Tablet mg. | |
|---|---|---|
| Series 1. (Placebo)* | A | B |
| Direct Compression Lactose | 235.6 | 235.6 |
| Calcium Sulfate, dihydrate | 94.5 | 94.5 |
| Starch | 17.5 (5%) | — |
| Chitin | — | 17.5 (5%) |
| Magnesium Stearate | 1.2 | 1.2 |
| Stearic Acid | 1.2 | 1.2 |
| Total Tablet Weight | 350.0 | 350.0 |
| 13/32" Standard Concave | | |
| Hardness: 5–7 Kg ± 0.5 Kg | | |
| Series 2. (Water-Soluble Drug) | C | D |
| Sodium Salicylate | 50.0 | 50.0 |
| Direct Compression Lactose | 280.1 | 280.1 |
| Starch | 17.5 (5%) | — |
| Chitin | — | 17.5 (5%) |
| Magnesium Stearate | 2.4 | 2.4 |
| Total Weight | 350.0 | 350.0 |
| 13/32" Standard Concave | | |
| Hardness: 5–7 Kg ± 0.5 Kg | | |
| Series 3. (Moderately Water-Soluble Drug) | E | F |
| Caffeine | 50.0 | 50.0 |
| Direct Compression Lactose | 280.1 | 280.1 |
| Starch | 17.5 (5%) | — |
| Chitin | — | 17.5 (5%) |
| Magnesium Stearate | 2.4 | 2.4 |
| Total Weight | 350.0 | 350.0 |
| 13/32" Standard Concave | | |
| Hardness: 5–7 Kg ± 0.5 Kg | | |
| Series 4. (Slightly Water-Soluble Drug) | G | H |
| Aspirin | 50.0 | 50.0 |
| Direct Compression Lactose | 280.1 | 280.1 |
| Starch | 17.5 (5%) | — |
| Chitin | — | 17.5 (5%) |
| Magnesium Stearate | 2.4 | 2.4 |
| Total Weight | 350.0 | 350.0 |
| 13/32" Standard Concave | | |
| Hardness: 5–7 Kg ± 0.5 Kg | | |
| Series 5. (Very Slightly Water-Soluble Drug) | I | J |
| Phenacetin | 50.0 | 50.0 |
| Direct Compression Lactose | 280.1 | 280.1 |
| Starch | 17.5 (5%) | — |
| Chitin | — | 17.5 (5%) |
| Magnesium Stearate | 2.4 | 2.4 |
| Total Weight | 350.0 | 350.0 |
| 13/32" Standard Concave | | |
| Hardness: 5–7 Kg ± 0.5 Kg | | |

*This series is not a control on the other series; it is presented solely for a comparison of starch with chitin.

TABLE II

TABLET COMPOSITION USED TO COMPARE THE DISINTEGRATION TIME, DISSOLUTION RATE, AND FRIABILITY TEST FOR CHITIN AND STARCH EMPLOYING THE WET GRANULATION METHOD

| | Quantity per Tablet, mg. | |
|---|---|---|
| Series 6 (Placebo)* | K | L |
| Lactose | 280.1 | 280.1 |
| Sucrose | 50.0 | 50.0 |
| Starch | 17.5 (5%) | — |
| Chitin | — | 17.5 (5%) |
| Magnesium Stearate | 2.4 | 2.4 |
| Total Tablet Weight | 350.0 | 350.0 |
| 13/32" Standard concave | | |
| Granulating solvent: Purified water | | |
| Hardness: 4–6 Kg ± 0.5 Kg | | |
| Series 7 (Water-Soluble Drug) | M | N |
| Sodium Salicylate | 50.0 | 50.0 |
| Lactose | 279.0 | 279.0 |
| Starch | 17.5 (5%) | — |
| Chitin | — | 17.5 (5%) |
| Magnesium Stearate | 3.5 | 3.5 |
| Total Tablet Weight | 350.0 | 350.0 |
| Granulating solvent: 20% Acacia Solution | | |
| 13/32" Standard concave | | |
| Hardness: 4–6 Kg ± 0.5 Kg | | |
| Series 8 (Moderately Water-Soluble Drug) | O | P |
| Caffeine | 50.0 | 50.0 |
| Lactose | 279.0 | 279.0 |
| Starch | 17.5 (5%) | — |
| Chitin | — | 17.5 (5%) |
| Magnesium Stearate | 3.5 | 3.5 |

TABLE II-continued
TABLET COMPOSITION USED TO COMPARE THE DISINTEGRATION TIME, DISSOLUTION RATE, AND FRIABILITY TEST FOR CHITIN AND STARCH EMPLOYING THE WET GRANULATION METHOD

|  | Quantity per Tablet, mg. | |
|---|---|---|
| Total Tablet Weight | 350.0 | 350.0 |
| Granulating solvent: 20% Acacia Solution | | |
| 13/32" Standard concave | | |
| Hardness: 4–6 Kg ± 0.5 Kg | | |
| Series 9 (Very Slightly Water-Soluble Drug) | Q | R |
| Phenacetin | 50.0 | 50.0 |
| Lactose | 279.0 | 279.0 |
| Starch | 17.5 (5%) | — |
| Chitin | — | 17.5 (5%) |
| Magnesium Stearate | 3.5 | 3.5 |
| Total Tablet Weight | 350.0 | 350.0 |
| Granulating solvent: 20% Acacia Solution | | |
| 13/32" Standard concave | | |
| Hardness: 4–6 Kg ± 0.5 Kg | | |

*This series is not a control on the other series; it is presented solely for a comparison of starch with chitin.

Relative Efficiency of Disintegrants in Various Tablet Formulations for Direct Compression The results indicate that chitin is a better disintegrant than starch. The ultimate manner in which disintegrants can be properly determined is to compare their effectiveness in tablets prepared for evaluating disintegration time, dissolution rate, and friability. Tablet formulations of various excipient composition and method of manufacture were employed to evaluate the relative efficiency of chitin and starch. The tablet formulation manufactured for each series maintained the same physical parameters as shown in Table I and Table II for series 1–9. The quantity of disintegrant was kept constant with each series for the purpose of material comparison. The 5 percent disintegrant was chosen based on the suggested percentage for starch. Tables III and IV summarized the disintegration time and friability as determined for the tablets prepared by direct compression.

TABLE III
DISINTEGRATION TIME FOR VARIOUS TABLET FORMULATIONS CONTAINING STARCH OR CHITIN MADE BY DIRECT COMPRESSION ETHOD

|  | Disintegration Time, min.* |
|---|---|
| Series 1. (Placebo) | |
| Formula A (5% starch) | 5.2 ± 0.3 |
| Formula B (5% chitin) | 4.1 ± 0.1** |
| Series 2. (Water-Soluble Drug) | |
| Formula C (5% starch) | 10.4 ± 0.7 |
| Formula D (5% chitin) | 8.8 ± 0.7** |
| Series 3. (Moderately Water-Soluble Drug) | |
| Formula E (5% starch) | 13.1 ± 1.0 |
| Formula F (5% chitin) | 13.5 ± 2.6** |
| Series 4. (Slightly Water-Soluble Drug) | |
| Formula G (5% starch) | 7.0 ± 1.0 |
| Formula H (5% chitin) | 11.8 ± 1.0** |
| Series 5. (Very Slightly Water-Soluble Drug) | |
| Formula I (5% starch) | 34.7 ± 3.9 |
| Formula J (5% chitin) | 15.3 ± 1.1** |

*Average of five individual tests; each test contains six tablets.
**A statistically significant difference at the 95% level.

TABLE IV
FRIABILITY FOR VARIOUS TABLET FORMULATIONS CONTAINING STARCH OR CHITIN MADE BY DIRECT COMPRESSION METHOD

|  | Friability, *% |
|---|---|
| Series 1. (Placebo) | |
| Formula A (5% starch) | 0.53 ± 0.24 |
| Formula B (5% chitin) | 0.52 ± 0.08 |
| Series 2. (Water-Soluble Drug) | |
| Formula C (5% starch) | 0.68 ± 0.13 |
| Formula D (5% chitin) | 0.28 ± 0.02** |
| Series 3. (Moderately Water-Soluble Drug) | |
| Formula E (5% starch) | 0.40 ± 0.07 |
| Formula F (5% chitin) | 0.35 ± 0.05 |
| Series 4. (Slightly Water-Soluble Drug) | |
| Formula G (5% starch) | 0.39 ± 0.05 |
| Formula H (5% chitin) | 0.34 ± 0.13 |
| Series 5. (Very Slightly Water-Soluble Drug) | |
| Formula I (5% starch) | 0.84 ± 0.16 |
| Formula J (5% chitin) | 0.60 ± 0.10 |

*Average of three individual tests.
**A statistically significant difference at the 95% level.

Series one formulation was a placebo tablet formulation. The disintegration time of the tablets containing chitin showed a significant difference from those containing starch. The friability did not show a significant difference between these two disintegrants.

Series two formulation tablets contained sodium salicylate, a water-soluble drug, as the active ingredient. These tablets which contain chitin disintegrated significantly faster than those which contained starch, and showed less friability and a higher dissolution rate.

Series five formulation tablets contained phenacetin, a very slightly water-soluble drug. The tablets which contained chitin also showed rapid disintegration, less friability, and a higher dissolution rate.

Series three formulation tablets contained caffeine, a moderately water-soluble drug. These tablets which contained chitin showed a slower disintegration time than those which contained starch, but they still showed less friability, and the dissolution rates of these two kinds of tablets were practically equal.

Series four formulation tablets contained aspirin, a slightly water-soluble drug. These tablets which contained chitin also showed a slower disintegration time than those which contained starch. The friability did not show significant difference between these two disintegrants. The dissolution rates of these two kinds of tablets were practically identical.

Relative Efficiency of Disintegrants in Various Tablet Formulations for Wet Granulation Method Tables V and VI summarized the disintegration and friability as determined for the tablets prepared by the wet granulation method. These tables indicate that chitin performed more effectively than starch as a tablet disintegrant in the preparation of tablets by the wet granulation method.

TABLE V

DISINTEGRATION TIME FOR VARIOUS TABLET FORMULATIONS CONTAINING STARCH OR CHITIN MADE BY WET GRANULATION METHOD

| | Disintegration Time, min.* |
|---|---|
| Series 6. (Placebo) | |
| Formula K (5% starch) | 61.8 ± 3.6 |
| Formula L (5% chitin) | 37.5 ± 2.4** |
| Series 7. (Water-Soluble Drug) | |
| Formula M (5% starch) | 85.6 ± 4.5 |
| Formula N (5% chitin) | 19.6 ± 2.9** |
| Series 8. (Moderately Water-Soluble Drug) | |
| Formula O (5% starch) | 49.7 ± 2.5 |
| Formula P (5% chitin) | 44.8 ± 2.0** |
| Series 9. (Very Slightly Water-Soluble Drug) | |
| Formula Q (5% starch) | >120 |
| Formula R (5% chitin) | 63.8 ± 2.8** |

*Average of five individual tests; each test contains six tablets.
**A statistically significant difference at the 95% level.

TABLE VI

FRIABILITY FOR VARIOUS TABLET FORMULATIONS CONTAINING STARCH OR CHITIN MADE BY WET GRANULATION

| | Friability, *% |
|---|---|
| Series 6. (Placebo) | |
| Formula K (5% starch) | 0.51 ± 0.06 |
| Formula L (5% chitin) | 0.35 ± 0.02** |
| Series 7. (Water-Soluble Drug) | |
| Formula M (5% starch) | 0.39 ± 0.03 |
| Formula N (5% chitin) | 0.36 ± 0.03** |
| Series 8. (Moderately Water-Soluble Drug) | |
| Formula O (5% starch) | 1.29 ± 0.18 |
| Formula P (5% chitin) | 0.55 ± 0.09** |
| Series 9. (Very Slightly Water-Soluble Drug) | |
| Formula Q (5% starch) | 0.93 ± 0.03 |
| Formula R (5% chitin) | 0.89 ± 0.01** |

*Average of three individual tests.
**A statistically significant difference at the 95% level.

TABLE VII

DISSOLUTION RATES OF SODIUM SALICYLATE IN 1000 ml. AQUEOUS SOLUTION AT pH 1.2 FOR TABLETS CONTAINING CHITIN OR STARCH PREPARED BY DIRECT COMPRESSION

| Disintegration | $t_{50\%}$, min. | $t_{75\%}$, min. | $t_{90\%}$, min. |
|---|---|---|---|
| Starch | 26.2 | >30 | >30 |
| Chitin | 19.1 | 24.1 | 29.7 |

TABLE VIII

DISSOLUTION RATES OF PHENACETIN IN 1000 ml. AQUEOUS SOLUTION AT pH 1.2 FOR TABLETS CONTAINING CHITIN OR STARCH PREPARED BY DIRECT COMPRESSION

| Disintegrant | $t_{50\%}$, min. | $t_{75\%}$, min. | $t_{90\%}$, min. |
|---|---|---|---|
| Starch | 19.8 | 28.9 | >30 |
| Chitin | 11.2 | 16.0 | 19.3 |

TABLE IX

DISSOLUTION RATES OF CAFFEINE IN 1000 ml AQUEOUS SOLUTION AT pH 1.2 FOR TABLETS CONTAINING CHITIN OR STARCH PREPARED BY DIRECT COMPRESSION

| Disintegrant | $t_{50\%}$, min. | $t_{75\%}$, min. | $t_{90\%}$, min. |
|---|---|---|---|
| Starch | 6.2 | 8.5 | 9.1 |
| Chitin | 4.2 | 6.8 | 9.1 |

TABLE X
DISSOLUTION RATES OF ASPIRIN IN
1000 ml. AQUEOUS SOLUTION
AT pH 1.2 FOR TABLETS
CONTAINING CHITIN OR STARCH
PREPARED BY DIRECT COMPRESSION

| Disintegration | $t_{50\%}$, min. | $t_{75\%}$, min. | $t_{90\%}$, min. |
|---|---|---|---|
| Starch | 7.9 | 13.1 | 24.7 |
| Chitin | 10.5 | 16.1 | 24.7 |

TABLE XI
DISSOLUTION RATES OF SODIUM
SALICYLATE IN 1000 ml. AQUEOUS
SOLUTION AT pH 1.2 FOR TABLETS
CONTAINING CHITIN OR
STARCH PREPARED BY WET GRANULATION METHOD

| Disintegrant | $t_{50\%}$, min. | $t_{75\%}$, min. | $t_{90\%}$, min. |
|---|---|---|---|
| Starch | >30 | >30 | >30 |
| Chitin | 12.7 | 22.0 | 28.9 |

TABLE XII
DISSOLUTION RATES OF PHENACETIN IN
1000 ml. AQUEOUS SOLUTION
AT pH 1.2 FOR TABLETS
CONTAINING CHITIN OR STARCH
PREPARED BY WET GRANULATION METHOD

| Disintegrant | $t_{50\%}$, min. | $t_{75\%}$, min. | $t_{90\%}$, min. |
|---|---|---|---|
| Starch | 27 | >30 | >30 |
| Chitin | 25 | 28.9 | >30 |

TABLE XIII
DISSOLUTION RATES OF CAFFEINE IN
1000 ml. AQUEOUS SOLUTION
At pH 1.2 FOR TABLETS
CONTAINING CHITIN OR STARCH
PREPARED BY WET GRANULATION METHOD

| Disintegrant | $t_{50\%}$, min. | $t_{75\%}$, min. | $t_{90\%}$, min. |
|---|---|---|---|
| Starch | 22 | >30 | >30 |
| Chitin | 20 | 30 | >30 |

Correlation of Disintegration and Dissolution Rates

The correlation of disintegration time and dissolution rate in this study cannot be established because some formulas such as series 3, 4, and 8 show different disintegration times but show almost equal rates of dissolution. These results are similar to those reported in the literature relative to the relationship between the disintegration time and dissolution rate. No absolute correlation has been established between the disintegration times and dissolution rates for tablets. Disintegration times of water-soluble drugs were found to be independent of the dissolution rate. Some reports showed disintegration times correlated with dissolution rates which depended on the characteristics of the drugs. It has been reported that when using calcium acetylsalicylate, buffered aspirin, and plain aspirin tablets, the amount dissolved in 10 minutes and the amount of the drug absorbed were inversely proportional to the disintegration time.

It is possible to have tablets disintegrate rapidly, yet the active drug may dissolve slowly. Fast disintegration does not guarantee availability, nor does slow disintegration indicate nonavailability. The formula for the preparation of tablets could be important relative to the correlation of the disintegration time and dissolution behavior.

The preceding results clearly reveal that pharmaceutical tablets containing chitin possess very highly beneficial disintegration properties. Chitin performed significantly better than starch as a tablet disintegrant in almost all of the drug formulations studied. In the others, it was at least as good as starch, which is known in the art as an eminently effective disintegrant. It has also been shown that chitin may have the ability to promote the dissolution rate of pharmaceutical tablets containing certain drugs.

Because of its ready accessibility, its very low cost, its recognized stability and compatibility, in view of its demonstrated superior efficiency as a disintegrant, chitin is a most desirable component for pharmaceutical tablets, and such tablets containing chitin will fulfill an important need in the art.

In the practice of the present invention, similar beneficial results are obtained, as expected, using primary derivatives of chitin, as exemplified by chitosan, which are considered equivalent to chitin and are to be comprehended in the use of the word "chitin".

Although the present invention has been described in detail with respect to certain preferred embodiments thereof, it is apparent to those of skill in the art that variations and modifications in this detail may be effected without any departure from the spirit and scope of the present invention, as defined in the hereto-appended claims.

What is claimed is:

1. A method of causing a pharmaceutical tablet to disintegrate upon being administered to an animal, which comprises administering to the animal a tablet fabricated from a mixture containing a pharmaceutically-active ingredient and a disintegratingly-effective amount of chitin.

2. The method of claim 1, wherein the chitin is present in the mixture in an amount sufficient to provide from about 2 to about 20 percent by weight.

* * * * *